(12) United States Patent
Mu et al.

(10) Patent No.: US 6,508,921 B1
(45) Date of Patent: Jan. 21, 2003

(54) LITHIUM ION-SELECTIVE ELECTRODE FOR CLINICAL APPLICATIONS

(75) Inventors: Xihai Mu, Chino Hills, CA (US); Chandra P. Jain, Placentia, CA (US)

(73) Assignee: Beckman Coulter, Inc., Fullerton, CA (US)

(*) Notice: Subject to any disclaimer, the term of this patent is extended or adjusted under 35 U.S.C. 154(b) by 0 days.

(21) Appl. No.: 09/534,464

(22) Filed: Mar. 24, 2000

(51) Int. Cl.$^7$ ............................................ G01N 27/333
(52) U.S. Cl. .............. 204/418; 210/500.28; 210/500.27
(58) Field of Search ................................ 204/418, 415, 204/296, 282, 290.1; 210/500.27, 500.28, 502.1

(56) References Cited

U.S. PATENT DOCUMENTS

| | | | |
|---|---|---|---|
| 4,454,007 A | * | 6/1984 | Pace ........................... 205/779 |
| 4,770,759 A | | 9/1988 | Young et al. ................ 204/418 |
| 5,192,417 A | * | 3/1993 | Oyama et al. ............... 204/418 |
| 5,240,573 A | * | 8/1993 | Carey ....................... 205/782.5 |

OTHER PUBLICATIONS

Sadaya Kitazawa et al "Lipophilic Crown—4 Derivatives as Lithium Ionophores". Abstract of *J. Amer.chem.Soc.* 1984, 106: 23 6978–6983.

* cited by examiner

*Primary Examiner*—Jill Warden
*Assistant Examiner*—Alex Noguerola
(74) *Attorney, Agent, or Firm*—Hogan & Hartson, LLP; William H. May; D. David Hill

(57) ABSTRACT

A lithium ion-selective membrane that favors the bonding of lithium and depresses sodium interference is invented by a charge balance approach. A lithium ion-selective electrode (Li-ISE) having the membrane of this invention demonstrates a fast kinetic response, good precision and reproducibility, high sensitivity and the ability to retain the sensitivity after a long-term contact with biological samples. The sensor shows Nernst linearity with a slope of 55.4 mV for lithium ion concentrations between 0.5 $\mu$mol/L and 10 mmol/L. The membrane includes at least about 2% by weight of 6,6-dibenzyl-1,4,8,11 tetraoxacyclotetradecane ionophore; from about 0.025% to about 1% by weight of potassium tetrakis(4-chlorophenyl)borate additive; a plasticizer; and a polymeric material.

12 Claims, 3 Drawing Sheets

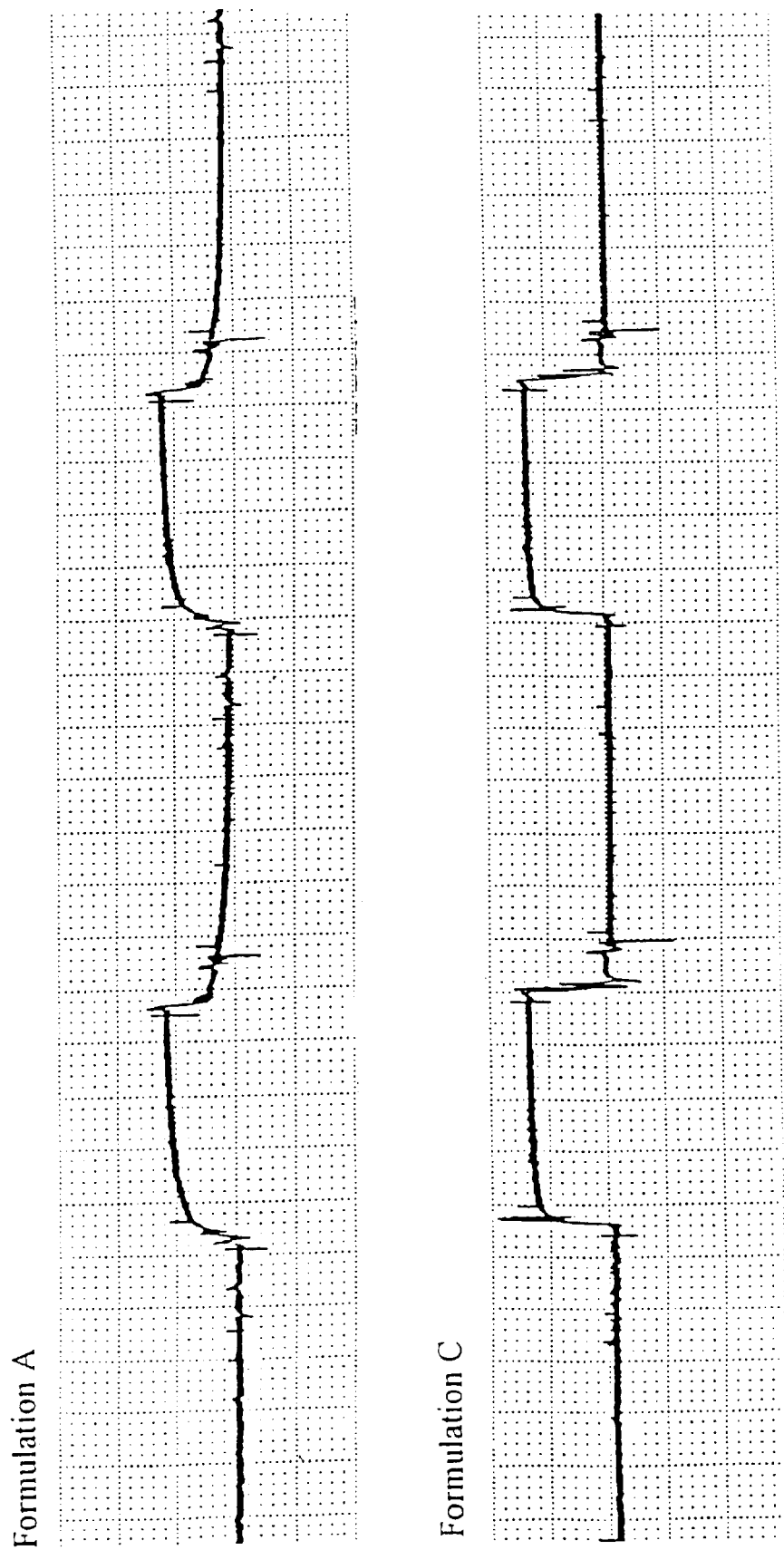

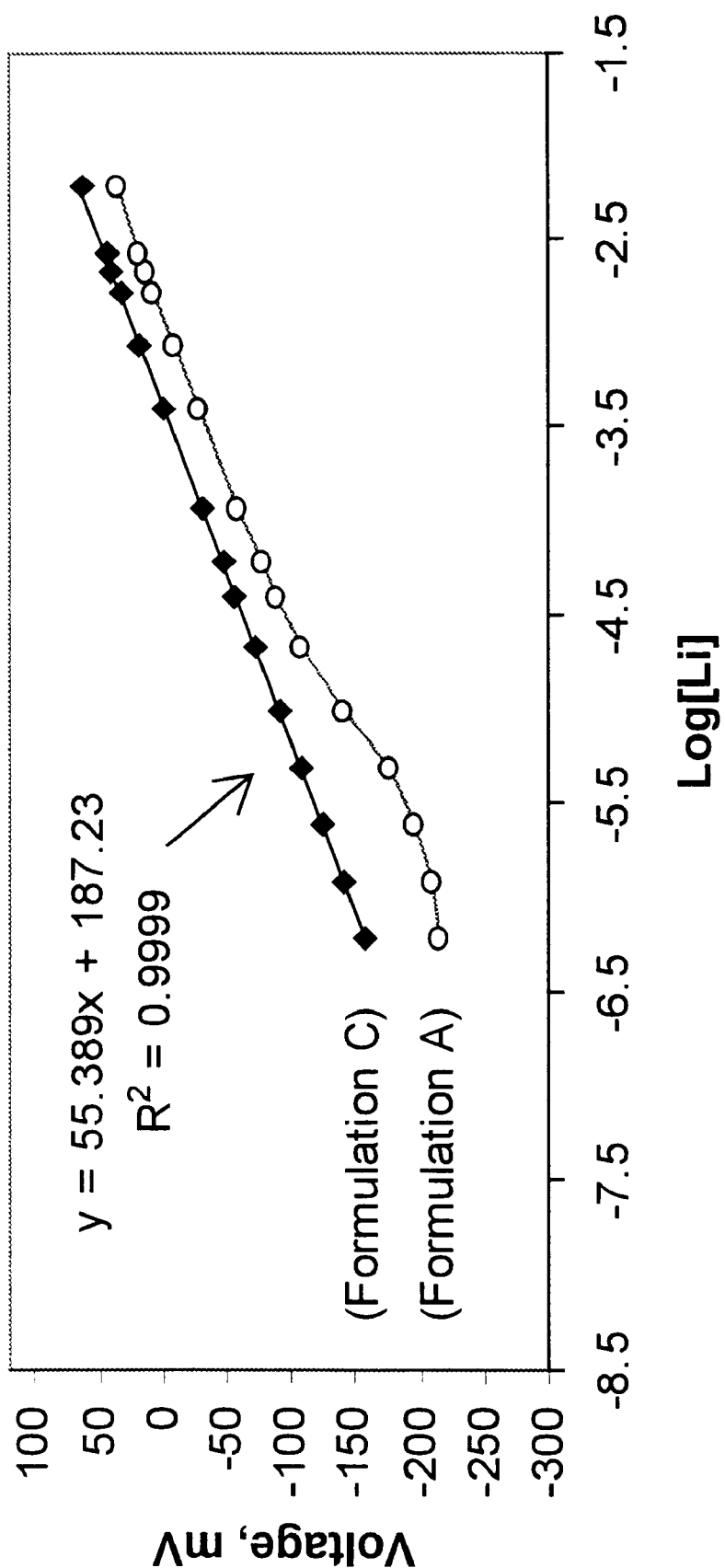
Figure 2. Lithium Electrode Linearity

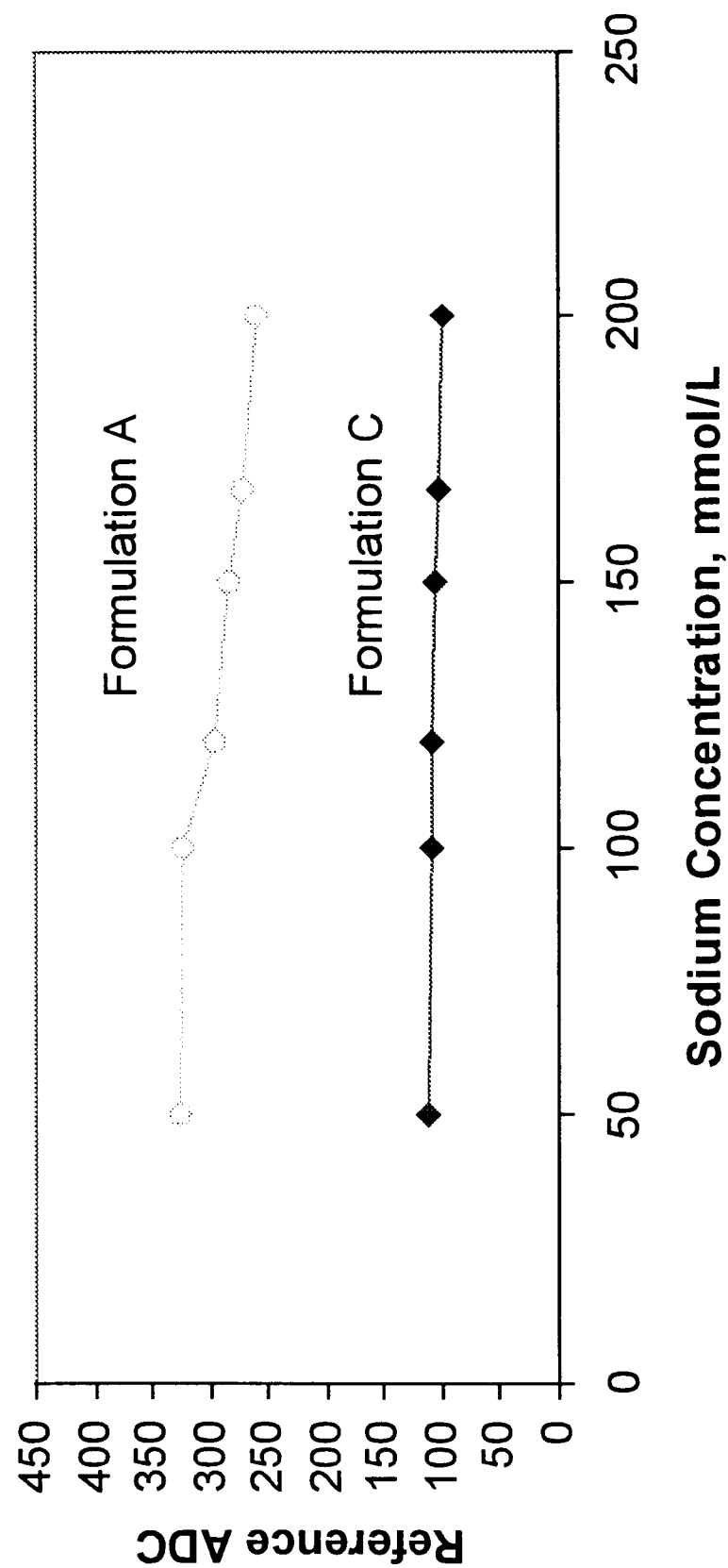

LITHIUM ION-SELECTIVE ELECTRODE FOR CLINICAL APPLICATIONS

BACKGROUND OF THE INVENTION

1. Area of the Art

This invention relates to a lithium ion-selective electrode for a potentiometric determination of a lithium ion concentration in liquid samples, particularly in clinical samples.

2. Description of the Prior Art

The use of lithium has become a widely accepted treatment of mental disorders, such as maniac depressive illness. Due to its toxicity, close monitoring of lithium concentration in biological fluids (e.g. sera, plasma, urine, spinal fluid, or whole blood) is required during the treatment. However, quantitative determination of lithium is hampered by the presence of other ionic compounds, in particular sodium ions, in such fluids. This interference is most noticeable at lower lithium concentrations (for example, about 0.10 mmol/l). Accordingly, there is a need for a convenient and highly sensitive method for a quantitative lithium analysis in clinical samples.

Various techniques and methods for the quantitative determination and measurement of lithium in a liquid test medium are known, but have been limited in the past, for the most part, to flame photometry. Despite its relative simplicity, flame photometry is a tedious procedure with high susceptibility to background interferences. Additionally, flammable gas utilized in this method presents a safety concern.

A potentiometric determination of a lithium ion concentration in clinical samples avoids many of these problems. Typically, devices for potentiometric measurements of lithium ion include a reference electrode and a lithium ion-selective electrode (Li-ISE). When the electrodes are simultaneously immersed into a sample solution, an electrical potential develops between them. This potential is proportional to the logarithm of the activity of the lithium ion. The logarithmic relationship between the potential and ionic activity in solution is described by the well-known Nernst equation. The electrical potential can be determined using a potentiometric measuring device, such as an electrometer.

Currently available Li-ISEs typically include a lithium ion-selective membrane formed of a lithium ion-selective carrier (lithium ionophore), an activator, a film-forming polymeric resin, and a plasticizer. The ionophore must be capable of sequentially complexing the lithium ion, transporting the complexed ion across the membrane, and releasing the ion, in preference to other cations present in the sample solution. Examples of such ionophores include crown ethers such as 14-crown-4-derivatives and 15-crown-4-derivatives (J. Am. Chem. Soc., 106 (1984), p. 6978), amide ethers (Anal. Chem., 58 (1986), p. 1948); polypropoxylate adducts (Analyst, 110 (1985), p. 1381); N,N'-diheptyl-N, N'-5,5-tetramethyl-3,7-dioxsanonane diamide (Helv. Chim. Acta, 69 (1986), page 1821 and J. Chem. Soc. Perkin Trans., II, (1986), p. 1945), a derivative of 1,10-phenanthroline (U.S. Pat. No. 4,861,455), and the like.

U.S. Pat. Nos. 4,214,968; 4,504,368; 4,770,759 describe Li-ISEs utilizing crown ethers as ionophores. However, many crown ethers are not adequately selective to lithium ions. For example, 1,5,9,13-tetramethyl-1,5,9,13-tetranonyl tetrafuro-16-crown-4-ether and dicyclohexyl-12-crown-4-ether exhibit unacceptable electrode drift and poor ion selectivity when used as lithium ionophores (U.S. Pat. No. 4,504,368). Therefore, selection of an ionophore and its concentration, and optimizing amounts of other additives in the membrane of Li-ISE are important for the optimum performance of the electrode (Anal. Chem. Acta, (1984), 156, p. 1).

The conventional Li-ISEs have significant limitations, including short lifetime and poor reproducibility. Conventional Li-ISEs lose their sensitivity and reliability, even with the most carefully preformed conditioning procedures, and start to exhibit non-Nernstian responses and substantial random drift. Another major drawback of currently available Li-ISE is their limited specificity (Anal. Chem. (1991), 63, p. 22850). This represents a major problem in view of 130–150 mmol/l of sodium typically present in patient serum and plasma samples. Protein, present in biological samples, also hinders performance of conventional Li-ISE membranes.

Conventional Li-ISEs, therefore, fail to provide ion-selective compositions and electrodes which are highly selective and sensitive to lithium ion, accurate, and long-lasting.

SUMMARY OF THE INVENTION

It is an object of the present invention to provide a novel Li-ISE membrane having high selectivity and specificity for lithium ions, fast kinetic response, good measuring precision, and a long life-time. It is a further object of the invention to provide a Li-ISE which retains sensitivity, precision, Nernst linearity, and reproducibility after long-term contact with biological samples and in the presence of competing species, such as sodium.

These and other objects are achieved in a lithium ion-selective membrane of the present invention comprising at least about 2% by weight of 6,6-dibenzyl-1,4,8, 11 tetraoxacyclotetra-decane ionophore and from about 0.05% to about 1% by weight of a potassium tetrakis(4-chlorophenyl) borate additive. The composition of the membrane further includes a plasticizer and a polymeric material.

The Li-ISE of the present invention has been found to provide a number of advantages. As explained in a greater detail below, these advantages include negligible affect of sodium and proteins present in the samples on measurements, even after exposure to more than 20,000 patient samples, fast response, and Nernst linearity of the signal at low lithium concentrations. The Li-ISE of this invention has a long life-time.

The Li-ISE of this invention system is well-suited for use with any analytical system, which relies on potentiometric determinations of lithium ion in fluids. Examples of such systems include, but are not limited to, SYNCHRON EL-ISE, SYNCHRON CX, and SYNCHRON LX20 clinical systems manufactured by Beckman Coulter, Inc. (CA).

The present invention is defined in its fullest scope in the appended claims and is described below in its preferred embodiments.

BRIEF DESCRIPTION OF THE FIGURES

The above-mentioned and other features of the present invention and the manner of obtaining them will become more apparent, and will be best understood, by reference to the following description, taken in conjunction with the accompanying drawings, in which:

FIG. 1 demonstrates typical traces of potential vs. time obtained using the Li-ISEs of the present invention (Formulations A and C).

FIG. 2 shows a logarithmic relationship between potential measured using the Li-ISEs of the present invention (Formulations A and C) and known activity of lithium ion in the solution.

FIG. 3 shows a relationship between reference ADC (Analog to Digital Conversion, a voltage measure) and sodium concentration in a sample obtained using the Li-ISEs of the present invention (Formulations A and C).

DETAILED DESCRIPTION OF THE EMBODIMENTS OF THE INVENTION

The present invention provides a lithium ion-selective membrane, which favors the lithium bonding and at the same time depresses interference from other cations, such as sodium. The membrane comprises a lithium ion-selective carrier (lithium ionophore), an additive, a film-forming polymeric resin, and a plasticizer.

The selectivity of an ion-selective electrode (ISE) for a particular ion is due to the chemical nature of the ionophore. Thus, the use of different chemical components as the ionophore provides different membranes for use in ISEs specific to different ions. The concentration of the ionophore in the membrane may vary depending upon the particular ionophore used, the ion undergoing analysis, the ionophore solvent, concentration of other additives, etc. Although a number of substances may be used as lithium ionophores, 6,6-dibenzyl-1,4,8,11 tetraoxacyclo-tetradecane was selected in one embodiment of the present invention for its high lithium specificity and stability. It has been discovered that a higher concentration of this ionophore favors an interaction between lithium ions and the membrane. This interaction results in a higher density of positive charge at the membrane-solution interface and, therefore, depresses the interference from other cations, such as sodium. In one embodiment the concentration of 6,6-dibenzyl-1,4,8,11 tetraoxacyclotetradecane is at least about 2% by weight, preferably at least about 5% by weight.

The additive helps to improve membrane conductivity. In one embodiment of this invention, tetrakis(4-chlorophenyl) borate (PTB) is chosen as such additive. We established that decreasing concentration of PTB in the membrane favors the interaction between lithium ions and the membrane, as demonstrated by higher sensitivity. It is a clear indicator that the presence of PTB in the membrane diminishes lithium bonding. However, as the concentration of PTB decreases, the impedance of the membrane increases from about 1 megaohm (formulation A) to about 5 megaohm (formulation C). Consequently, in one embodiment, the concentration of PTB in the membrane was optimized to be from about 0.025% to about 1% by weight, preferably about 0.1% by weight.

Polymeric film-forming resins for use in the lithium ion-selective membrane of the instant invention include any of the hydrophobic natural or synthetic polymers capable of forming thin films of sufficient permeability. Examples of such polymeric resins include, but are not limited to, polyvinyl chloride (PVC), vinylidene chloride, acrylonitrile, polyurethanes, copolymers of polyvinyl chloride and polyvinylidene chloride, polyvinyl butyral, polyvinyl formal. In one embodiment of the invention, PVC is used as a film-forming resin. The concentration of PVC in the membrane-forming mixture is controlled to prevent its interference with electrochemical properties of the membrane. In the preferred embodiment, the concentration of PVC in the membrane is from about 30% to about 40% by weight.

The plasticizer serves as a solvent for the ionophore and provides ion mobility and transfer in the membrane. Substantially any ionophore solvent, which is compatible with the polymeric material and permits rapid wetting of the membrane by an aqueous sample, may be used. At the same time, the solvent must be sufficiently insoluble in water, so it does not migrate significantly into an aqueous sample. It is preferred that the solvent also serves as a plasticizer for the polymeric material. Examples of useful solvents include, but are not limited to, aromatic and aliphatic ethers, phosphates, mixed aromatic aliphatic phosphates, adipates, and mixtures thereof. In one embodiment of the present invention, a mixture of plasticizers 2-Nitrophenyloctylether (NPOE) and trioctylphosphate (TOP) is used. In the preferred embodiment, the amount of NPOE is from about 40% to about 60% by weight and the amount of TOP is from about 5% to 15% by weight, preferably, the amount of NPOE is about 50% by weight and the amount of TOP is about 9% by weight.

EXAMPLES

The following examples are presented for the purpose of illustration and are not intended to limit the scope of this invention.

Example I (Membrane Formulation)

Three membrane formulations, A–C, were used (Table 1). PTB and TOP solutions were made by dissolving them separately in cyclohexanone at room temperature to obtain 5.2% and 0.52% PTB solutions and 10% TOP solution. 10% PVC solution was made by dissolving PVC in cyclohexanone at 50° C. under constant inversion. Then, the required amount of the ionophore was dissolved in a mixture of PTB and TOP solutions. After the ionophore completely dissolved, the required amounts of NPOE and PVC solution were added to the ionophore solution and were mixed for at least 30 minutes with the use of an inverter.

TABLE 1

| Membrane Formulation | | | |
|---|---|---|---|
| | A | B | C |
| Ionophore | 0.05 g | 0.15 g | 0.15 g |
| 5.2% PTB solution | 0.45 g | 0.45 g | — |
| 0.52% PTB solution | — | — | 0.45 g |
| 10% TOP solution | 2.56 g | 2.56 g | 2.56 g |
| NPOE | 1.33 g | 1.33 g | 1.33 g |
| 10% PVC solution | 10.4 g | 10.4 g | 10.4 g |
| Relative Sensitivity | 1.00 | 1.74 | 2.08 |

The body of each Li-ISE was made of graphite and a connecting cable. The sensing surface of the body was about 12 mm$^2$. The sensing surface was treated with $KI/KI_3$ solution before membrane coating to increase voltage reading stability. The membrane was formed by applying 20 µl of the formulation solution to the sensing surface of the electrode. After about 80% of the solvent evaporated, another 20 µl of the formulation solution was placed on top. The cycle was repeated one more time (total of 60 µl of the formulation solution was used to form the membrane). The membrane was then air-dried for at least 72 hours before use.

We found that the performance of the sensor was particularly sensitive to the ionophore and PTB concentration/ratio in the membrane.

Example II (Sensitivity)

Table I lists the relative sensitivity of sensors made of the three formulations. Increasing the concentration of ionophore from 0.05 to 0.15 grams, or from about 2% to 5% by weight, (A to B) resulted in an increase in sensitivity by 74%. Decreasing the concentration of PTB, from about 0.8% by weight in B to about 0.08% by weight in C, added another 34% increase in sensitivity of the Li-ISE. Based on these results, formulation C was chosen as a preferred embodiment of the invention.

Example III (Kinetics of the Membrane Response)

The electrode's kinetic behavior for formulations A and C is shown in FIG. 1. Li-ISE of formulation C showed a very fast electrode response (less than 5 seconds), while Li-ISE of formulation A had a sluggish kinetic response (more than 20 seconds).

Example IV (Linearity of the Response)

Li-ISE with the membrane formed according to the formulation C showed excellent Nernst linearity (FIG. 2). It exhibited a log[Li$^+$] vs. voltage linearity with a slope of 55.4 mV and R$^2$=0.9999 for lithium concentration between 0.5 $\mu$mol/l and 10 mmol/l. Poor linearity was observed for Li-ISE with the membrane of formulation A.

Example V (Sodium Interference)

Sodium is the primary interfering cation for Li-ISE measurements in patient samples. FIG. 3 shows the dependence of reference ADC (a voltage measure) on sodium concentration on Beckman Coulter's EL-ISE clinical system. A very stable reference ADC reading was seen for an electrode made of formulation C. Reference ADC drift was seen for the electrode with the membrane of formulation A.

Example VI (Correlation to a Reference Method)

The concentration of lithium in patient samples was measured with flame photometry (X) and Beckman Coulter's EL-ISE clinical system with the Li-ISE of this invention (Y) (Table 2).

TABLE 2

Correlation Results

|  | X-mean | Y-mean | Slope | Intercept | R | N |
|---|---|---|---|---|---|---|
| Formulation A | 0.652 | 0.746 | 0.928 | 0.140 | 0.991 | 55 |
| Formulation C | 0.688 | 0.702 | 1.047 | −0.018 | 0.992 | 56 |

The lithium concentration measurements conducted with Li-ISE having the membrane of formulation C correlated well with the measurements made with the flame photometry method. However, the lithium concentration measurements conducted with Li-ISE having the membrane of formulation A showed results about 15% higher than those from the flame photometry method.

Example VII (Precision)

Table 3 lists precision results for formulation C. The sensor showed excellent precision.

TABLE 3

Precision Results

| Sample | Mean, mmol/L | n | SD, mmol/L | CV |
|---|---|---|---|---|
| Sample 1 | 0.59 | 21 | 0.0084 | 1.4 |
| Sample 2 | 1.64 | 21 | 0.0051 | 0.31 |
| Sample 3 | 2.69 | 20 | 0.0091 | 0.34 | n is number of separate measurements; SD is standard deviation; CV is coefficient of variance, CV was calculated as SD/Mean × 100.

Example VIII (Protein Effect)

Li-ISEs with a membrane of formulation C showed negligible protein effect after more than three months in contact with biological samples on Beckman Coulter's clinical systems. Electrodes with the membrane made of formulation A were more sensitive to protein effect as was indicated by a sensitivity drop (data not shown).

Example IX (Life-time)

Li-ISEs with a membrane of formulation C remained their sensitivity and reliability for more than three months when used with Beckman Coulter's EL-ISE clinical systems. The Li-ISEs with membranes formulated according to the formulation A lasted only from a few days to a few weeks before losing their sensitivity.

What is claimed is:

1. A lithium ion-selective membrane, comprising:

6,6-dibenzyl-1,4,8,11 tetraoxacyclotetradecane ionophore;

potassium tetrakis(4-chlorophenyl)borate additive; and a plasticizer comprising a mixture of 2-Nitrophenyloctylether and trioctylphosphate.

2. The lithium ion-selective membrane in accordance with claim 1, comprising at least about 2% of the ionophore by weight.

3. The lithium ion-selective membrane in accordance with claim 1, comprising about 0.1% of the additive by weight.

4. The lithium ion-selective membrane in accordance with claim 1, further comprising a polymeric material.

5. The lithium ion-selective membrane in accordance with claim 4 wherein the polymeric material is a high molecular polyvinyl chloride.

6. The lithium ion-selective membrane in accordance with claim 5, wherein the amount of the high molecular polyvinyl chloride is from about 30% to about 40% by weight.

7. The lithium ion-selective membrane in accordance with claim 1, wherein the amount of 2-Nitrophenyloctylether is from about 40% to about 60% by weight.

8. The lithium ion-selective membrane in accordance with claim 1, wherein the amount of trioctylphosphate is from about 5% to about 15% by weight.

9. The lithium ion-selective membrane in accordance with claim 1, wherein the amount of 2-Nitrophenyloctylether is about 50% by weight and the amount of trioctylphosphate is about 9% by weight.

10. A lithium ion-selective electrode, comprising:

a lithium ion-selective membrane, wherein the membrane comprises 6,6-dibenzyl-1,4,8,11 tetraoxacyclotetradecane ionophore; potassium tetrakis (4-chlorophenyl) borate additive; and a plasticizer comprising a mixture of 2-Nitrophenyloctylether and trioctylphosphate; and a solid body.

11. The lithium ion-selective electrode in accordance with claim 10, wherein the solid body is made of graphite.

12. The lithium ion-selective electrode in accordance with claim 10, wherein the electrode demonstrates Nernst linearity for lithium ion concentrations between about 0.5 $\mu$mol/12 and 10 mmol/1.

* * * * *